United States Patent [19]

Linner et al.

[11] Patent Number: 5,044,165

[45] Date of Patent: * Sep. 3, 1991

[54] CRYO-SLAMMER

[75] Inventors: John G. Linner; Stephen A. Livesey; Carmen Piunno; Mark Zaltsberg, all of Woodlands; Frank Gibson, Spring, all of Tex.

[73] Assignee: Board of Regents, The University of Texas, Austin, Tex.

[*] Notice: The portion of the term of this patent subsequent to Feb. 28, 2006 has been disclaimed.

[21] Appl. No.: 284,989

[22] Filed: Dec. 15, 1988

Related U.S. Application Data

[63] Continuation-in-part of Ser. No. 102,395, Sep. 29, 1987, which is a continuation-in-part of Ser. No. 989,701, Dec. 3, 1986, Pat. No. 4,707,998.

[51] Int. Cl.$^5$ .............................................. B01D 8/00
[52] U.S. Cl. ...................................... 62/55.5; 62/275; 118/50.1
[58] Field of Search ................... 62/55.5, 275, 514 R, 62/275, 78, 265, 268; 118/50.1; 34/92, 5

[56] References Cited

U.S. PATENT DOCUMENTS

| | | | |
|---|---|---|---|
| 2,672,032 | 3/1954 | Towse | 62/126 |
| 3,067,589 | 12/1962 | Dennis et al. | 62/293 |
| 3,125,096 | 3/1964 | Antiles et al. | 128/401 |
| 3,679,450 | 7/1972 | Beightol | 117/3 |
| 3,745,290 | 7/1973 | Harnden, Jr. | 219/10.49 |
| 3,928,566 | 12/1975 | Briggs et al. | 424/94 |
| 3,932,943 | 1/1976 | Briggs et al. | 34/5 |
| 3,942,519 | 3/1976 | Shock | 128/24 |
| 3,982,541 | 9/1976 | L'Esperance | 128/303.1 |
| 4,030,314 | 6/1977 | Strehler et al. | 62/65 |
| 4,055,904 | 11/1977 | Horne | 34/45 |
| 4,056,855 | 11/1977 | Kelman | 3/13 |
| 4,063,068 | 12/1977 | Johnson et al. | 219/441 |
| 4,090,374 | 5/1978 | Faust et al. | 62/341 |
| 4,100,158 | 7/1978 | Hydes et al. | 544/225 |
| 4,120,991 | 10/1978 | Ornstein et al. | 427/2 |
| 4,122,853 | 10/1978 | Smith | 128/303.1 |
| 4,197,658 | 4/1980 | Fraser | 34/92 |
| 4,201,319 | 5/1980 | Andera et al. | 222/396 |
| 4,232,453 | 11/1980 | Edelmann | 34/92 |
| 4,266,111 | 5/1981 | Trillwood | 219/121 |
| 4,269,713 | 5/1981 | Yamashita et al. | 210/500.2 |
| 4,278,623 | 7/1981 | Niegisch | 264/28 |
| 4,278,701 | 7/1981 | Von Hagens | 427/4 |
| 4,302,950 | 12/1981 | Sitte | 62/514 |
| 4,321,117 | 3/1982 | Kaetsu et al. | 204/159.16 |
| 4,331,591 | 5/1982 | Baylis | 260/112.5 |
| 4,336,691 | 6/1982 | Burnstein et al. | 62/64 |
| 4,337,240 | 6/1982 | Saklad | 424/1 |

(List continued on next page.)

FOREIGN PATENT DOCUMENTS

| | | |
|---|---|---|
| 0136014 | 3/1985 | European Pat. Off. |
| 2704300 | 8/1977 | Fed. Rep. of Germany |
| 2739796 | 3/1979 | Fed. Rep. of Germany |
| 3042578 | 6/1982 | Fed. Rep. of Germany |
| 614532 | 11/1979 | Switzerland |

OTHER PUBLICATIONS

Med-Vac, Inc. "Cryopress" (brochure).
Usukura J. and Yamada, E., "Freeze-Etching Technique with Simple Rapid Freezing of Fresh Biological Specimen," Journal of Electron Microscopy, vol. 29 (1980), pp. 376–382.
Hosoi et al., "Freeze Drying Apparatus and its Application of Adenovirus Journal of Electron Microsscopy", vol. 28 (1979) pp. 49–50.

(List continued on next page.)

Primary Examiner—Henry A. Bennet
Attorney, Agent, or Firm—Arnold, White & Durkee

[57] ABSTRACT

A method and apparatus for ultrarapid cooling of tissue samples against a chilled cryogenic surface. The cryogenic surface is enclosed in a high vacuum chamber during cooling of the cryogenic surface. Dry non-condensable room temperature gas is introduced from an external source to raise the chamber pressure just prior to slamming or plunging a sample against the cryogenic surface. The cryogenic surface is heated for regeneration or cleaning purposes between each successive sample.

30 Claims, 8 Drawing Sheets

U.S. PATENT DOCUMENTS

| | | | |
|---|---|---|---|
| 4,347,671 | 9/1982 | Dias et al. | 34/15 |
| 4,379,003 | 4/1983 | Robbins et al. | 148/104 |
| 4,423,600 | 1/1984 | McKenna | 62/62 |
| 4,428,821 | 1/1984 | Van Dellen | 264/135 |
| 4,449,305 | 5/1984 | Baron et al. | 34/92 |
| 4,489,569 | 12/1984 | Sitte | 62/514 |
| 4,510,169 | 4/1985 | Linner | 427/4 |
| 4,551,992 | 11/1985 | Sitte et al. | 62/514 |
| 4,559,298 | 12/1985 | Fahy | 435/1 |
| 4,563,883 | 1/1986 | Sitte | 62/514 |
| 4,567,847 | 2/1986 | Linner | 118/50.1 |
| 4,569,850 | 2/1986 | Harris et al. | 426/482 |
| 4,578,963 | 4/1986 | Sitte | 62/514 |
| 4,580,411 | 4/1986 | Orfitelli | 62/371 |
| 4,580,416 | 4/1986 | Sitte | 62/514 |
| 4,619,257 | 10/1986 | Linner et al. | 128/303.1 |
| 4,676,070 | 6/1987 | Linner | 62/64 |
| 4,688,387 | 8/1987 | Conaway | 62/78 |
| 4,707,998 | 11/1987 | Linner et al. | 62/349 |
| 4,742,690 | 5/1988 | Linner | 62/264 |
| 4,757,689 | 7/1988 | Bachler et al. | 62/55.5 |
| 4,807,442 | 2/1989 | Linner et al. | 62/55.5 |

OTHER PUBLICATIONS

Katoh, M. et al., "A Freeze Drying Method for a Sample Substituted with a Fifty Percent Acetonitrile Aquatic Solution with a Metal Block for Drying," Journal of Electron Microscopy, vol. 29 (1980), pp. 197–198.

Morioka, H. et al., "A Simple Freeze Drying Method for Electron Microscopy of Bacteriophages," Journal of Electron Microscopy, vol. 29 (1980).

Escaig, J. "New Instruments which Facilitate Rapid Freezing at 83K and 6K", Journal of Microscopy, vol. 126 (Jun. 1982), pp. 221–229.

Boyne, A. F., "A Gentle, Bounce-Free Assembly for Quick Freezing Tissues for Electron Microscopy: Application to Isolated Torpedine Ray Electrocytre Stacks", Journal of Neuroscience Methods, 1 (1979), pp. 353–364.

Coulter, H. D., "Freezing and Drying of Biological tissues with a Toggle-Link Helium Freezer and an Improved Freeze-Drying Apparatus: Application to Neuropeptide Immunocytochemistry", Journal of Electron Microscopy, vol. 4 (1986), pp. 315–358.

Escaig, J., "Control of Different Parameters for Optimal Freezing Conditions", Science of Biological Specimen Preparation, pp. 117–122.

Handley, D. et al., "The Design and Use of a Simple Device for Rapid Quench-Freezing of Biological Samples", Journal of Microscopy (Mar. 1981), pp. 273–282.

Moor, H. et al., "The Influence of High Pressure Freezing on Mammalian Nerve tissue", Cell and Tissue Research (1980) pp. 201–216.

Terracio, L. and Schwabe, K. G., "Freezing and Drying of Biological Tissues for Electron Microscopy", Journal of Histochemistry and Cytochemistry, vol. 29 (1981), pp. 1021–1028.

Sleytr, U. B. and Robards, Replication: W., "Understanding the Artefact Problem in Freeze-Fracture replication: A Review", Journal of Microscopy, vol. 126 (1982), pp. 101–122.

Linner, jet al., "A New Technique for Removal of Amorphous Phase Tissue Water Without Ice Crystal Damage; A Preparative Method for Ultrastructural Analysis and Immunoelectron Microscopy", Journal of Histochemistry and Cytochemistry, vol. 34 (1986), pp. 1123–1135.

Linner et al., Cryopreparation of tissue for Electron Microscopy (Mar. 1985), pp. 165–174.

Livesey, S. A. and Linner, J. G., "Cryofixation Taking on a New Look", Nature, vol. 327 (May 21, 1987).

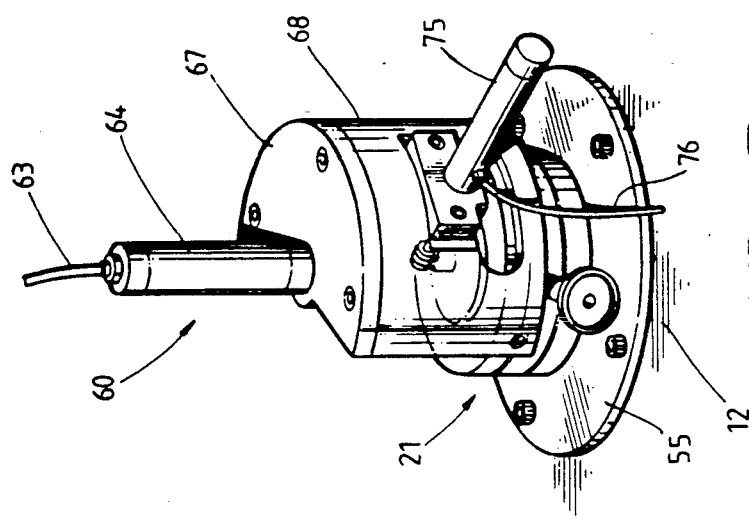
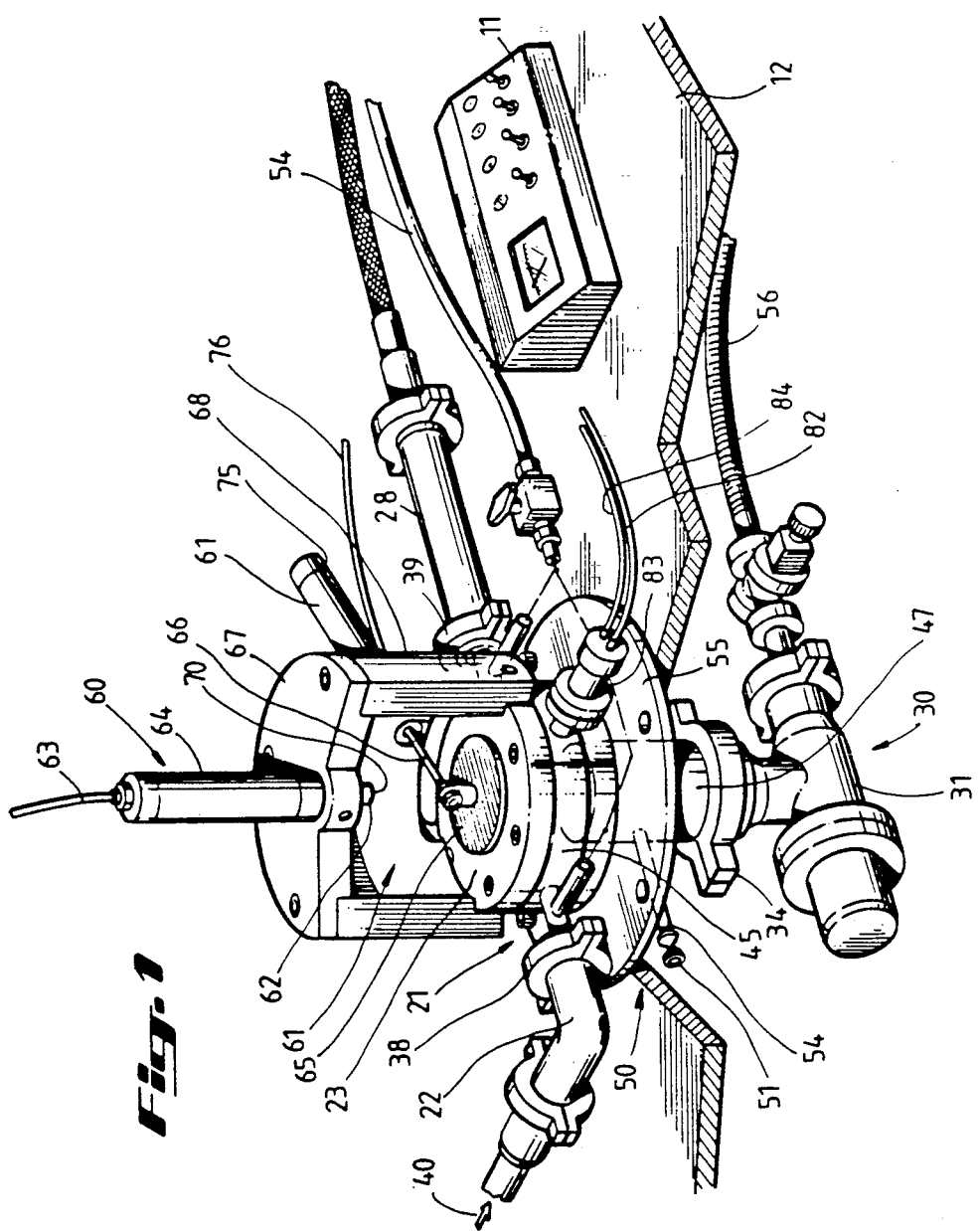

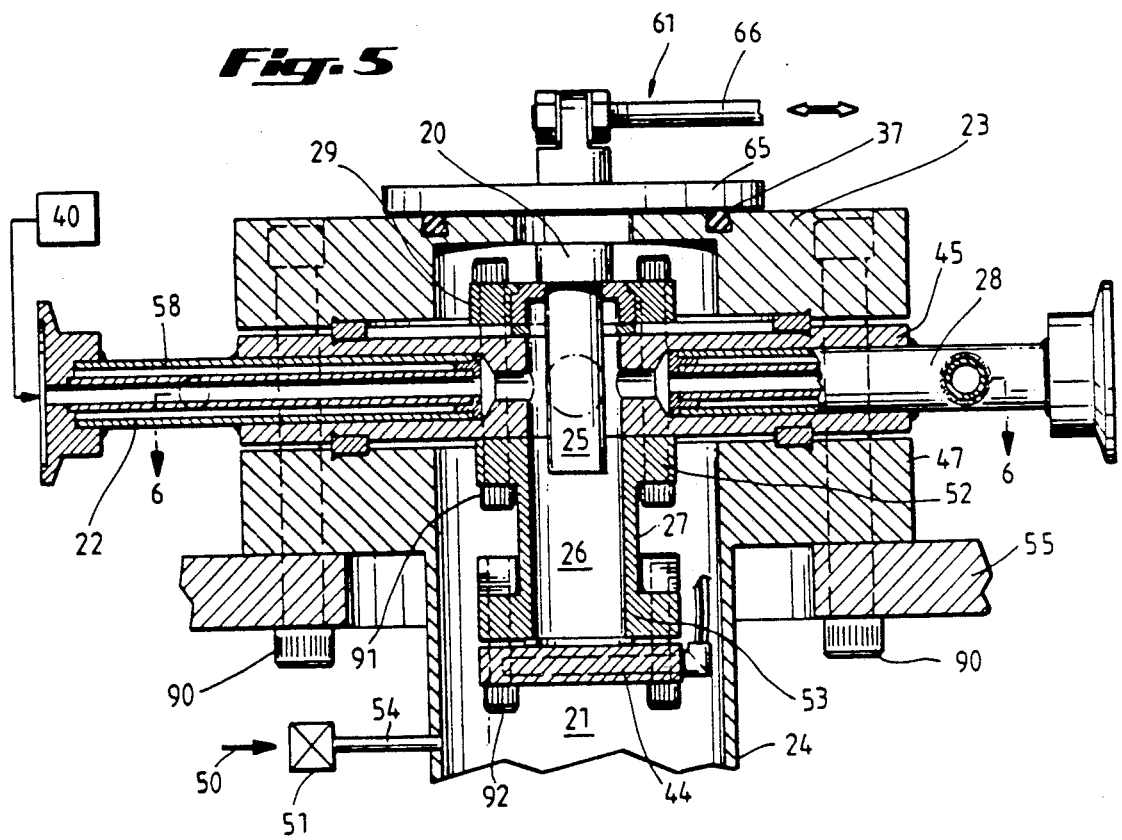
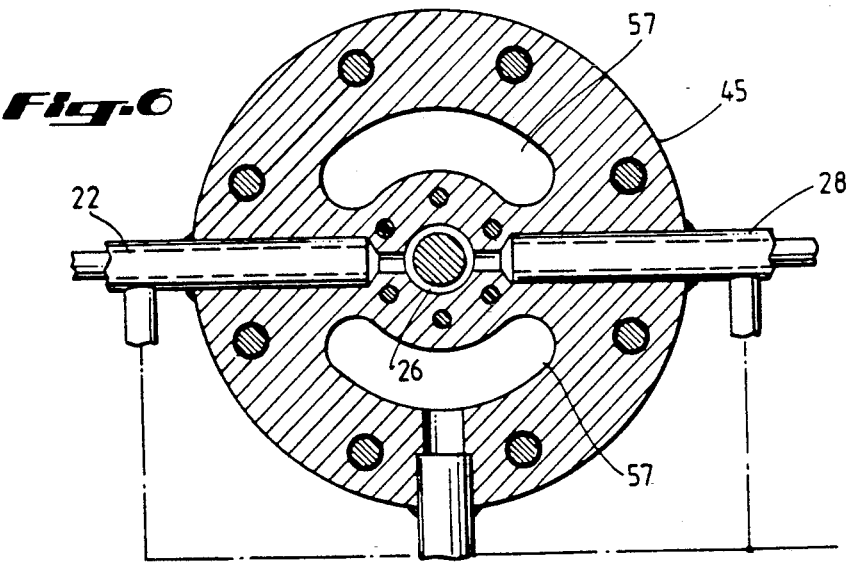

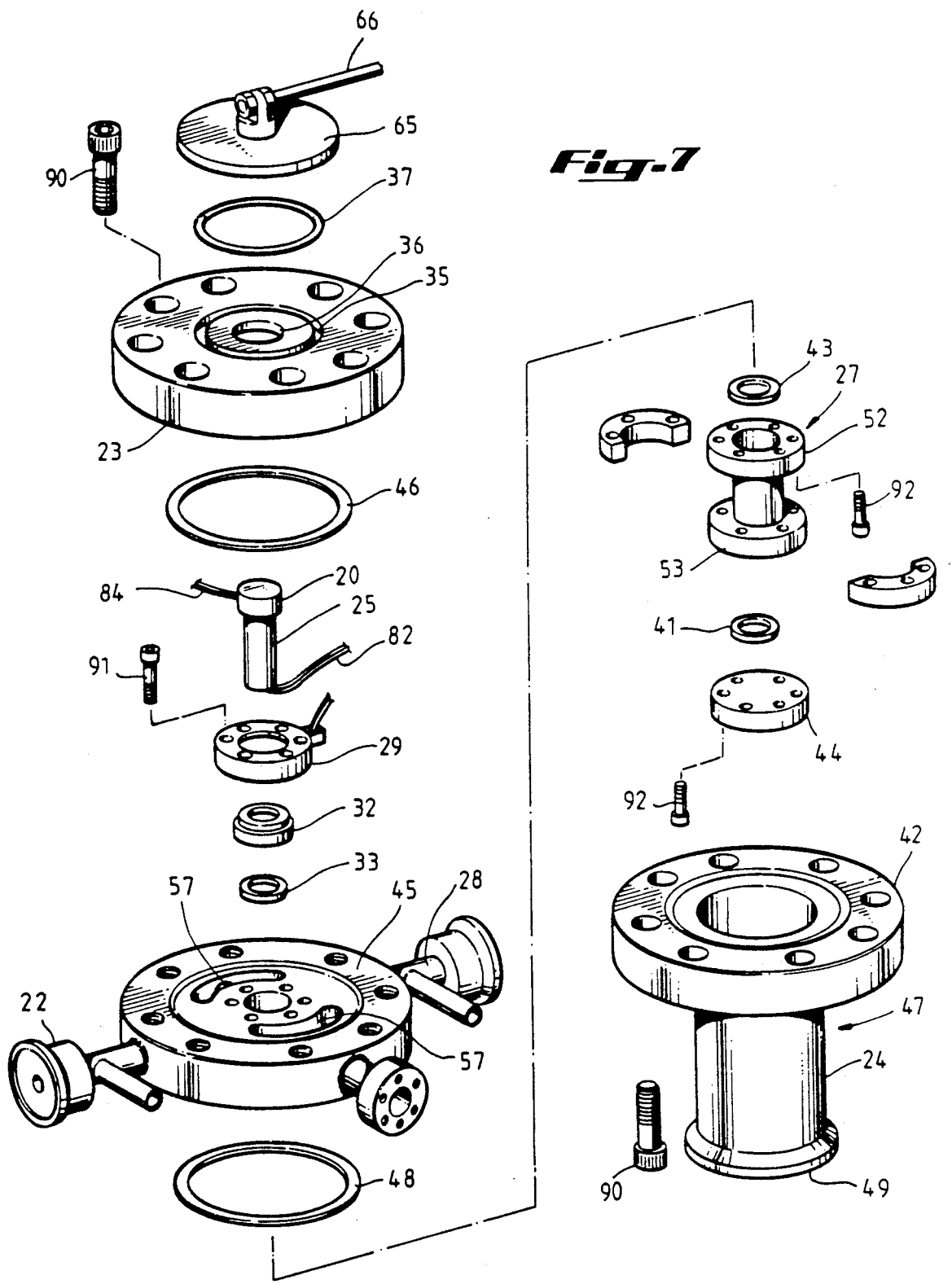

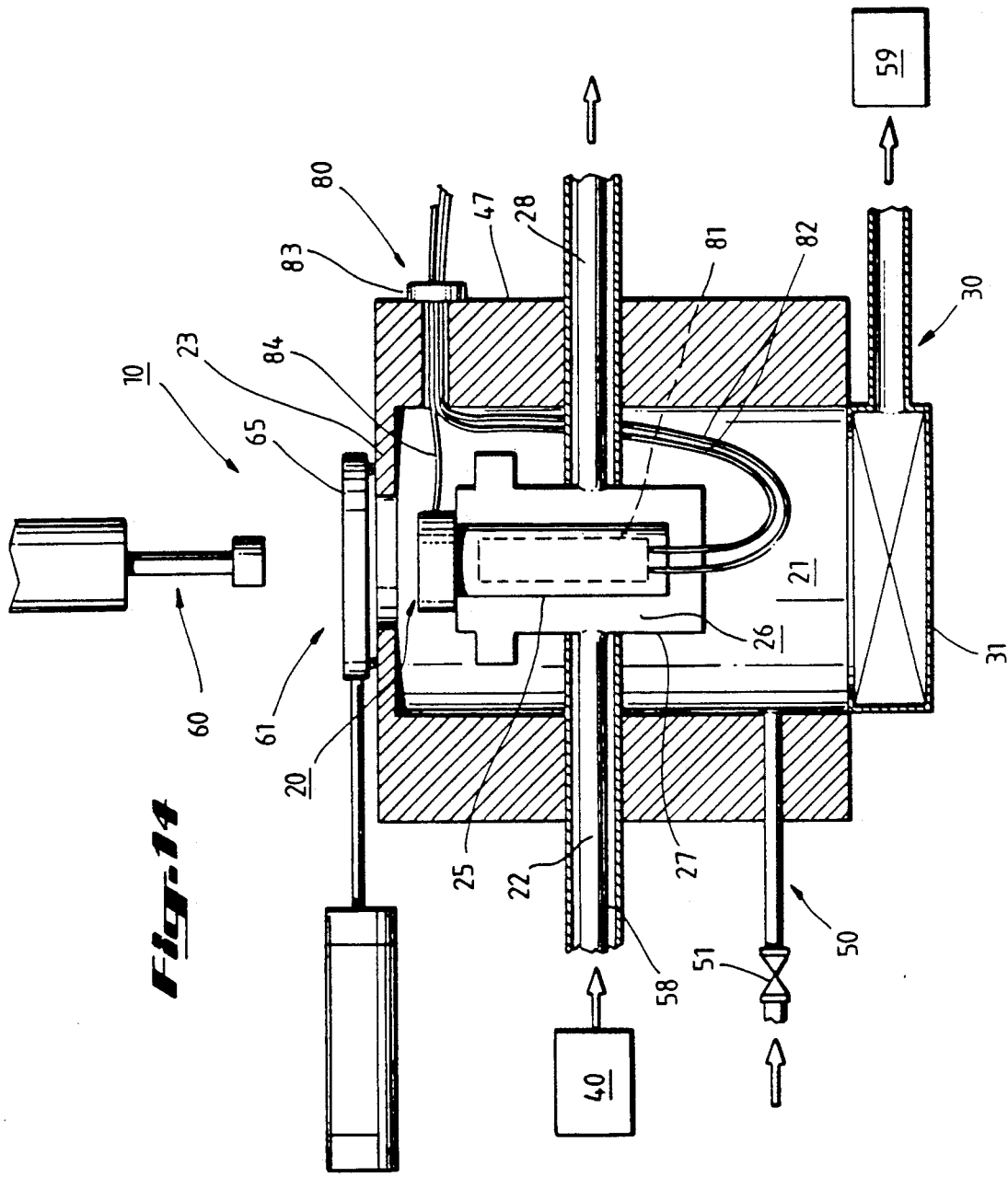

CRYO-SLAMMER

CROSS-REFERENCE TO AND INCORPORATION BY REFERENCE OF RELATED APPLICATION

This application is a continuation-in-part of commonly-assigned, copending U.S. patent application Ser. No. 102,395 filed Sept. 29, 1987, which in turn is a continuation-in-part of U.S. patent application Ser. No. 989,701 filed Dec. 3, 1986 now U.S. Pat. No. 4,707,998. The subject of said application Ser. Nos. 102,395 and 989,701 are hereby incorporated by reference.

BACKGROUND OF THE INVENTION

1. Field of the Invention

This invention relates to cryo-fixation apparatus and method for the ultrarapid cooling of biological samples. Ultrarapid cooling is a preparatory step to the cryo preparation of biological samples in apparatus such as that described in commonly assigned U.S. Pat. Nos. 4,510,169 and 4,567,847 issued to John G. Linner and commonly referred to as "The Linner Process" or "The Linner Apparatus". It is well known in the medical arts that to examine biological samples and determine the cellular structure and function thereof, the samples must be "fixed" with minimal alteration of ultrastructural integrity prior to the application of nearly all analytical methodologies. The apparatus of this invention can be used to ultrarapidly cool biological samples without the formation of resolvable ice crystals so that the ultrastructural integrity of the sample is not altered. In samples of a biological material that are more than a few microns in thickness the ice crystals will usually range in size from amorphous at the leading edge to hexagonal in the interior of the tissue. There is a gradient effect during the formation of ice crystals.

The terms "biological material", "biological samples", "tissue samples", "tissue specimens", and "biological tissue" are used throughout this disclosure to refer to samples that can be ultrarapidly cooled by the method and apparatus of this invention. The terms are used interchangeably and are not intended as a limitation on the functional capability of the method or apparatus disclosed herein. The terms should be understood to include small tissue samples appropriate for microscopic examination and larger tissue masses such as corneas which are appropriate for transplantation. The terms should be understood to include any material composed of one or more cells, either individual or in complex with any matrix or in association with any chemical; and to include any biological or organic material and any cellular subportion, product or by-product thereof. The terms should be further understood to include without limitation sperm, eggs, embryos, blood components and other cellular components. The contemplated utility of the apparatus of this invention is not limited to specific types or sizes of tissue, rather it should be understood to refer to any biological material derived from cells (including prokaryotic, eukaryotic, plant or animal), viral particles and the like. The apparatus of this invention can be designed or adapted to any size, shape or type of cellular tissue. Therefore, the terms "tissue", "tissue specimen(s)" and "tissue sample(s)" are used interchangeably and are not limiting on the uses to which the method and apparatus of this invention can be placed.

Although the method and apparatus of this invention are preferably used as a preliminary step in the cryopreparation of biological samples for ultrastructural analysis, i.e. electron microscopy, it should be understood that this is not intended as a limitation on the utility of the apparatus and method of this invention. To the contrary, the ultrarapid cooling method and apparatus of this invention have demonstrated utility in any area in which the ultrastructure of cellular components is desirably maintained in an unaltered state. Examples of such utility include, but are not limited to, electron microscopy, tissue preservation, tissue and organ transplants and various analytical and diagnostic methodologies. Therefore, although the method and apparatus of this invention are typically described in relationship to electron microscopy this should be understood not to be a limiting factor on the utility of the invention.

Although the examination of tissue by use of various microscopes or related magnifying apparatus has been practiced for many years, there has been an inherent problem in preparing tissue for use with contemporary high resolution analytical microscopes, such as the STEM electron microscopes, which permit the examination of sample constituents via X-ray analysis at powers of from 500× to 500,000× with point to point resolution of 2 to 3 Angstrom units. It is difficult to interpret the results of tissue analysis while concomitantly assessing the extent of various artifacts produced during the tissue preparation processes. It is thus essential that artifacts be avoided wherever possible. The term "artifact" refers to a product of artificial character due to extraneous agency. Another problem results from physical shrinkage of the tissue sample itself, which results in alteration of ultrastructure and massive rearrangement of infrastructural resolution.

During the so-called "Golden Age of Morphology" the predominant underlying goal in qualitative and quantitative microscopy has been an aesthetically pleasing image. This goal is readily attainable with the fixation methods and apparatus which are currently available. However, it has become essential that the aesthetically pleasing image, which is produced by the preparation process, also yield a tissue sample which accurately reflects the true condition of tissue in the living organism, i.e., approaching the "living state." This is the problem which is addressed and solved by the Linner TM Apparatus and Linner Process TM. One essential step in the preparation process is the cryopreparation or cryofixation procedure (as opposed to the freezing procedure). The cryo-preparation method and apparatus of this invention results in the preparation of tissue samples which are readily usable in known magnification and analytical apparatus.

In currently known cryopreparation and freeze-drying devices and methods, problems and limitations are encountered in attempts to rapidly cool the tissue sample without physically harming the sample. If the temperature decrease in the sample to its full depth does not take place at a sufficiently rapid rate, artifacts appear, the ultrastructural integrity of the sample may be damaged and the sample will not appear in its "living state". The prior art has therefore attempted to achieve a rapid rate of temperature decrease to the full depth of the sample, in order to minimize such damage.

Although the primary thrust of this application is in the preparation of tissue samples for analysis by current magnification apparatus, the invention is not intended to be so limited. More specifically, the "preparation" of tissue should be understood to refer to preparation of tissue for analysis as well as the cryofixation of tissue in anticipation of transplantation, modification, in vitro or in vivo cellular growth, fertilization, animated suspension or the more typical resin impregnation, setting, infiltration and analysis. The apparatus of this invention can be used to prepare tissue for any medical or analytical procedure without the ultrastructural damage previously thought to be inevitable in cryopreparation.

The apparatus of this invention is to be distinguished from contemporary freeze-drying apparatus. Freeze-drying is a technique which is well known in the art together with the equipment necessary to implement such freeze-drying. See, for example, U. S. Pat. No. 4,232,453. Although in certain freeze-drying techniques liquid nitrogen is used as a cooling medium, the tissue or sample itself does not attain such temperature. Freeze-drying normally contemplates sample temperatures of −50° C. to −80° C. In contrast, the ultrarapid cooling step of the cryopreparation process of the Linner Process TM and apparatus contemplate sample temperatures of −175° C. or colder. Therefore, for purposes of this application the terms "cryopreparation" and "cryofixation" are used in distinction to conventional "freezing" technology.

2. Description of the Related Art

The most common prior art method for preparation of tissue samples for analysis is by means of chemical fixation and organic solvent dehydration. Inherent in prior art processes is the concomitant artifact creation, sample shrinkage and resultant damage to and modification of tissue characteristics. These tissue characteristic modifications, whether in the form of artifacts or the like, require interpretation by the individual or apparatus analyzing or evaluating the sample. This introduces, in many instances, an unsatisfactory risk of error. Chemical fixation is a well known technique and has served the analytical biologist well for many years and undoubtedly will continue to do so in certain limited applications. However, as the use of tissue sample analysis becomes more complex and the use of such analysis becomes more widespread, alternatives to chemical fixation are demanded. This is especially true as advances are being made in the magnification and analytical apparatus which are available. It is necessary that tissue preparation methods and the apparatus necessary to prepare tissue samples be equally advanced as the analytical tools, i.e., electron microscopes, which are being used to analyze the samples. Obviously, if the technology for tissue sample preparation is inferior to the technology of microscopy then the advanced microscopes cannot be used to full advantage by the morphologist or other tissue examiner.

Similarly, it is essential that cryopreparation methods and apparatus develop concurrently with other medical technology, i.e., surgical transplant techniques, bioengineering and biogenetics. In short, cryo-preparation is an essential intermediate step in evolving processes using or analyzing cells or tissue. If cryo-preparation apparatus does not evolve then the thrust of medical technology into unexplained and unexplored medical arts will be blunted. The apparatus of this invention represents the cryopreparation breakthrough that will permit research into the use and preparation of biological tissue to keep pace with other advances in medical technology. The ultrarapid cooling apparatus of this invention provides the mechanism for eliminating the problems associated with available cryofixation apparatus.

An alternative to chemical fixation and organic solvent dehydration is freeze-drying cryofixed samples. Freeze-drying following cryofixation is a well documented and well known technique for tissue preservation. It has several advantages. Cryofixation results in a near-instantaneous arrest of cellular metabolism. There is also a stabilization and retention of soluble cell constituents through elimination of solvent contact with the sample. These are significant advantages to cryofixation freeze-drying that have resulted in a great deal of research in attempting to apply cryofixation and freezed-rying techniques to known tissue preparation processes.

Unfortunately, freeze-drying technology inherently possesses a number of disadvantages relevant to tissue preparation methodologies. The primary disadvantage in currently available freezing techniques and apparatus is the inherent formation of ice crystals. As can be readily appreciated, the formation of ice crystals destroys the ultrastructural integrity of the tissue sample being reviewed. The image is distorted and the cytoplasm becomes reticulated. The formation of ice crystals in the sample can also result in a change in pH within microcompartments of the tissue (eutectic formation) which possibly can result in abnormal tertiary conformation of macromolecules. There is also the possibility that proteins will denature and precipitate. These are but a few of the disadvantages which are inherent in conventional freezing/freeze-drying processes.

This general topic is discussed in some detail together with other prior art methods in an article entitled "Freezing and Drying of Biological Tissues for Electron Microscopy", Louis Terracio and Karl G. Schwabe, published in *The Journal of Histochemistry and Cytochemistry*, Volume 29, No. 9 at pp. 1021–1028 (1981). Problems associated with artifact formation are described in "Understanding the Artefact Problem in Freeze-Fracture Replication: A Review", *The Royal Microscopial Society*, (1982) at pp. 103–123.

A general principle found applicable to freezing techniques, which has demonstrated utility in the preparation of tissue samples, is that as the cooling rate increases, tissue fluids can be "vitrified" without the separation of water to extracellular spaces. The term "vitrified" or "vitrification" refers to the cryopreparation of tissue samples without the formation of resolvable ice crystals within the cellular structure. It has been postulated that regardless of the rate of cooling, ice crystals may still be formed, but as the cooling rates increase the size of the intracellular ice crystals decreases. The small size or absence of ice crystals at high freeze rates is of course a substantial advantage in morphology retention as this results in minimal artifact creation and minimal ultrastructural alteration or damage during tissue dehydration. The apparatus of this invention provides the ultrarapid cooling of one or more tissue samples to the vitreous phase in less than one second. The ultrarapid cooling according to the present invention is followed by dehydration of the tissue sample while in the state of reduced partial pressure of water vapor without substantial ultrastructural damage to the tissue cells.

Historically, the criteria by which the techniques for rapid supercooling have been judged was not the cooling rate of the system but simply the temperature of the environment in which the tissue was frozen. Thus, the term rapid supercooling has been applied to any system in which the supercooling agent has a temperature of −150° C. or below. The effectiveness of a cooling system, however, is dependent upon the rate at which heat is removed from the sample. Heat transfer is dependent not only on the temperature of the freezing system but also on its physical and thermal characteristics, as well as the size and thermal characteristics of the tissue.

The most commonly used technique for rapid supercooling is to immerse or "quench" the sample in a fluid cooling bath. The most commonly used fluids for quenching are liquid nitrogen, isopentane, propane and fluorocarbons such as Freon 12 and Freon 22. Although liquid nitrogen is generally regarded as an ideal quenching fluid due to its low temperature (−196° C.), there are inherent disadvantages in the use of liquid nitrogen due to the occurrence of tissue surface film boiling caused at least in part by the low heat of vaporization of liquid nitrogen. Film boiling is a characteristic of liquid nitrogen that inhibits the heat transfer rate by actually insulating the sample.

An alternative method for rapid supercooling is applying the tissue sample to the polished surface of a cryogenically cooled material such as the surface of a chilled metal block. This typically involves opposing the tissue sample to a polished flat metal surface by pressing it firmly against the surface of the metal. Silver and copper are typically used as the polished metal blocks. This method is designed to take advantage of the high thermal conductivities and heat capacities of these metals when cooled to liquid nitrogen or liquid helium temperatures. The critical step in chilling on the surface of a metal is making firm contact with the dry, chilled metal surface with no rotational, translational or rebounding motion. Certain commercially available apparatus having known utility in the medical arts address and provide "bounce-free" freezing. Credit for the development of this apparatus is generally accorded to Dr. Alan Boyne of the University of Maryland School of Medicine.

The Boyne apparatus and method included one or more copper bars partially submerged in a container filled with liquid nitrogen at −196° C. The end of the copper bar was a mirror-finished smooth cryogenic surface, and the thermal conductivity of copper enabled the surface to be cooled. Cold nitrogen gas from vaporization of the liquid nitrogen, which escaped past the end of the copper bar, helped to reduce the contaminants on the cryogenic surface. A tissue sample was then dropped by gravity against the surface. To reduce the bounce of the sample against the surface, the Boyne sample delivery assembly employed a weight dampening system utilizing glycerol to absorb the impact. Each copper bar must be cleaned after slamming a sample. The drawbacks of the Boyne apparatus included problems of hydrocarbon contamination and condensation on the cryogenic surface, inability to eliminate all bounce or vibration between the sample and surface, undesirable precooling of the sample with escaping nitrogen gas, and delays for cleaning and regenerating the cryogenic surface of the copper bars between each sequential sample. The Boyne method and apparatus thus could not reliably provide tissue samples with good ice crystal-free zones nor was it capable of properly vitrifying the samples beyond a depth of 10 to 15 microns.

Further development of freezing tissue samples against a metal block has been credited to Jacques Escaig of Paris, France. The method and apparatus of Escaig is described in "Control of Different Parameters For Optimal Freezing Conditions", Jacques Escaig, published in *Science of Biological Specimen Preparation,* at pp. 117–122 (1984). The Escaig apparatus also is disclosed in Swiss Patent No. 614,532, French Patent No. 2,337,878 and German Patent No. 2,700,196. Escaig provided several significant features not shown in earlier methods or devices for vitrifying tissue against a metal block. The Escaig method and apparatus cool a copper block with liquid helium, rather than liquid nitrogen, in order to increase the cooling rate of a tissue sample or specimen. Escaig disclosed that the average thickness of ice crystal-free zones in the tissue sample were much larger when the copper block was cooled by liquid helium rather than liquid nitrogen. Additionally, Escaig pointed out that the factors influencing the freezing process, independent of the tissue sample itself, are thermal contact between the specimen and metal block, condition of the block surface, specimen slipping, sample holder bounce and sample holder contact strength. Escaig obtained some control of these factors by utilizing a vacuum pump to keep the metal block under vacuum of $1 \times 10^{-3}$ mbar until just before slamming the specimen against the block, in order to reduce contamination on the block surface. Escaig also utilized an electromagnet to bring the specimen in contact with the block in order to improve mechanical contact between the specimen and the block.

According to the Escaig apparatus and method, a copper block is enclosed in a vacuum chamber. The chamber is then evacuated to approximately $1 \times 10^{-3}$ mbar with an external vacuum pump system. After a vacuum is reached in the chamber, Escaig employed an external nonreusable cryogen source—liquid helium pumped from a reservoir—to cool the copper block. The liquid helium is transmitted to a passage adjacent to the block through a conduit in the vacuum chamber. When the block is cooled to the desired temperature, Escaig used an electropneumatic system to open a stem insert in the liquid helium passage for releasing cold helium gas for several seconds into the vacuum chamber itself. The cold helium gas admitted into the vacuum chamber is obtained from vaporization of the liquid helium which was used to cool the metal block. The cold helium gas raises the pressure inside the vacuum chamber. When atmospheric pressure is reached inside the vacuum chamber, a shutter providing access to the vacuum chamber is spring biased to open the chamber and activate downward movement of a sample delivery assembly, which plunges or slams the tissue sample through the shutter opening and against the block. Opening of the shutter also triggers closing of the stem insert to stop the release of cold helium gas into the chamber.

Several problems have been encountered in the Escaig apparatus. Because Escaig used cold helium gas to bring the vacuum chamber up to atmospheric pressure, a tissue sample precools for approximately 15 milliseconds as it descends through a layer of cold helium gas at atmospheric pressure prior to plunging or slamming against the metal block. The precooling effect of the Escaig device is undesirable due to unwanted effects, such as ice crystal formation, on the physiology of the tissue sample. Additionally, movement of liquid helium and helium gas through the vacuum chamber inevitably resulted in vibration of the metal block, which was undesirable because it reduced or prevented good mechanical contact between the specimen and block.

Escaig's use of nonreusable liquid helium to cool the block further has proved to be expensive, somewhat unsafe and cumbersome due to the necessity of recooling the entire liquid helium system between each tissue sample. The end result was extremely slow turnover time for regenerating the copper block between each sample. Additionally, cleaning the block in the Escaig apparatus proved difficult because of condensation on the block forming after a sample was slammed against the block. To remove the condensation, pressurized nitrogen gas and hot air could be applied against the block. However, removal of the block for repolishing or other cleaning required disassembly of the vacuum chamber itself. Even if the block was not removed, the problems in regenerating the block surface resulted in a turnover time between samples which is commercially unacceptable. It was therefore not possible to use the Escaig device if a large number of sequential samples was desired.

The cryopreparation apparatus and method according to the present invention solves the problems inherent in the prior art including the Escaig apparatus and method. The present invention addresses the problems in the prior art of slow turnover time between the vitrification of tissue samples, by enabling several samples to be vitrified sequentially. The present invention also solves the problems in the prior art caused by undesirable precooling of the tissue sample or specimen before contact with the cryogenic block, cleaning and reheating the cryogenic block between each sample, and removal of the cryogenic block from the apparatus.

SUMMARY OF THE INVENTION

The apparatus and method of the present invention provide for the cryo-slamming (i.e., ultrarapid cooling or vitrification) of tissue samples by slamming or plunging the samples against a chilled cryogenic block. The upper portion of the cryogenic block is a highly polished and mirror-finished face or "cryo-slam" surface and the lower portion is a thermally conductive tubular "cryofinger". The cryo-slam surface can be removed from the cryofinger for cleaning or replacement with an alternate cryo-slam surface. The apparatus contemplates interchanging cryo-slam surfaces to vary surface area, surface shape, and the material composition of the cryo-slam surface. The apparatus contemplates chilling of a tissue sample against the mirror-finished smooth cryo-slam surface. The cryogenic block is enclosed within an evacuatable chamber. Under certain circumstances an ultra-high hydrocarbon free vacuum chamber may be used. For purposes of this application the terms "ultra-high vacuum" and "high vacuum" are used interchangeably although it is recognized that there are technical distinctions.

In the preferred embodiment, the shutter opening to the vacuum chamber and the movement of the tissue sample on the plunger are pneumatically controlled in order to assure precise timing of the shutter and plunger, with a constant rate of descent. Noncondensable dry inert gas at room temperature is introduced into the chamber just prior to pneumatically activating the shutter and plunging the sample against the block. The introduction of a dry inert gas which is noncondensable at cryogenic temperatures enables the chamber pressure to be raised and the shutter to be opened without undesirable condensation on the cryo-slam surface, or dehydration and precooling of the tissue sample during its downward movement through the shutter opening towards the cryo-slam surface. An external source is used to supply the dry inert gas to the chamber. The inert gas may be selected from dry nitrogen or a noble gas such as dry helium, and the like.

In the preferred embodiment, the cryo-slam surface may be regenerated rapidly between slamming of successive samples. The rapid regeneration is enabled by the use of a heating unit enclosed within the cryofinger. The heating unit is activated between samples to heat the cryo-slam surface for cleaning and removing condensation.

Before a sample is slammed against the cryo-slam surface, a hydrocarbon-free vacuum must be obtained in the vacuum chamber surrounding the cryogenic block. The cryo-slam surface is then cooled with a liquid cryogen system which circulates a coolant such as liquid nitrogen or helium through a cooling jacket. The cooling jacket which is enclosed within the vacuum chamber, jackets the thermally conductive cryofinger portion of the cryogenic block. The detachable cryo-slam surface is located at the top of the cryofinger which extends below the top of the cooling jacket and is sealed in relation thereto. Dry nitrogen or helium gas is then introduced into the vacuum chamber to bring the pressure to atmospheric before the slamming operation takes place. The present invention enables sequential vitrification of tissue samples against the cryo-slam surface without substantial delays for regeneration inherent in the prior art and facilitates rapid recooling.

Another advantage of the apparatus of this invention is the ability to cryoprepare tissue specimens without overt disruption or destruction of the morphological characteristics of the ultrastructure of tissue cells. The cryo-slamming method and apparatus of the present invention provide for ultrarapid cooling of tissue samples so that the tissue may be dehydrated while maintained in the solid, vitreous phase without creating unnecessary artifacts which restrict interpretation by conventional analytical apparatus.

The cryo-slamming apparatus and method of the present invention may demonstrate an extraordinary application in the transplanting of corneal tissue. Prior to this invention attempts to transplant corneas which involved a necessary freezing or freeze-drying of the corneas after removal from the donor invariably resulted in a clouded cornea upon transplanting. The clouding remained for from as little as several days to the life of the transplanted cornea. This physical condition of the transplanted cornea was caused by ice crystal formation in the cornea itself and concomitant damage to the stroma. Use of the apparatus of this invention has enabled ophthalmologists to cryoprepare corneas and to then transplant those corneas to recipients with virtually negligible clouding or crystal formation. The ability to so transplant corneas represents an exceptional advantage to the process of this invention as well as a medical breakthrough in corneal transplant surgery. In a preferred embodiment, the cryo-slam surface is generally semispherical in shape and adapted to receive a cornea.

DESCRIPTION OF THE DRAWING

FIG. 1 is a perspective view of a preferred embodiment of the cryo-slamming apparatus according to the present invention.

FIG. 2 is a perspective view of the vacuum chamber and delivery assembly according to a preferred embodiment of the present invention.

FIG. 5 is a cross-sectional view of the vacuum chamber according to a preferred embodiment of the present invention.

FIG. 6 is a cross-sectional view of the conduit housing according to a preferred embodiment of the present invention, taken along section line 6—6 of FIG. 5.

FIG. 7 is an exploded perspective view of the vacuum chamber according to a preferred embodiment of the present invention.

FIG. 14 is a schematic drawing of the components of this invention demonstrating the functional relationship of the elements.

DETAILED DESCRIPTION OF THE PREFERRED EMBODIMENT

Figure 3:
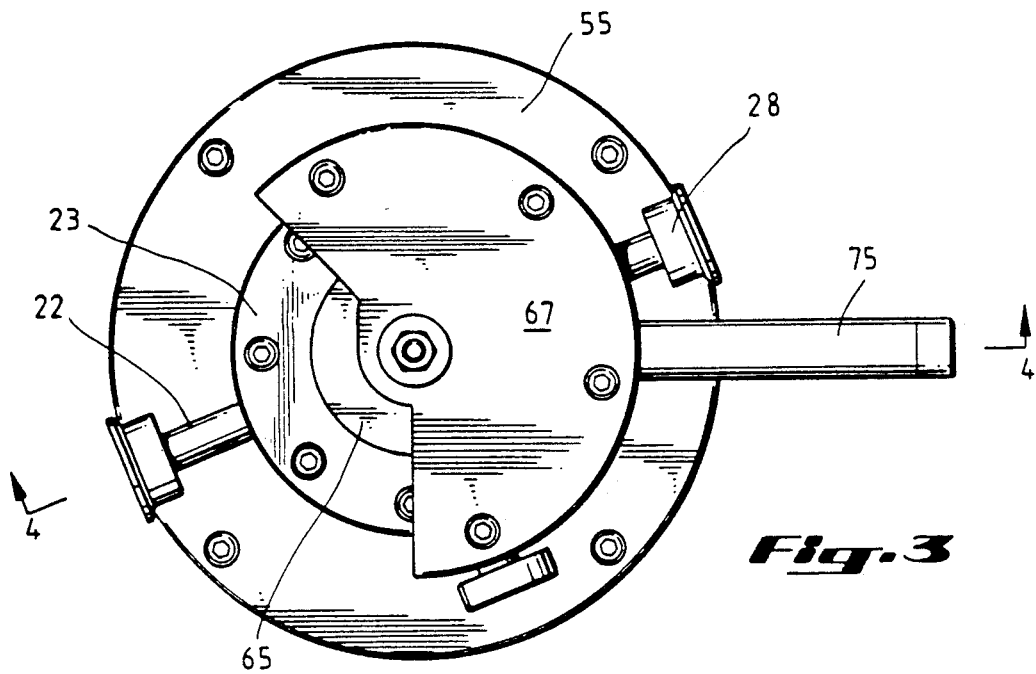
FIG. 3 is a top view of the vacuum chamber according to a preferred embodiment of the present invention.

In the apparatus of this invention it is a fundamental prerequisite that the desired biological material is obtained. Tissue specimens or samples are collected by a variety of means, i.e., surgical extraction, withdrawn blood samples, binders and any of a variety of other techniques which are well known and conventional. The particular method of obtaining a sample of a particular biological material is not limiting on the apparatus of this invention. However, the preparation of tissue specimens in the apparatus of this invention is enhanced if the tissue specimens are processed as soon after excising as is possible.

The preparation of a tissue specimen takes place immediately as it is received. The sample cannot be retained in a fixative, i.e., formaldehyde, or another biologically active stabilizing solution, in an attempt to maintain the sample during shipping, storage or other necessary operations. It is also critical that the sample not be routinely frozen or otherwise physically modified prior to preparation according to the method of this invention. The sample may later be physically sectioned or otherwise physically prepared for long-term storage in apparatus or use with various currently available commercial analytical apparatus.

In one application of this invention a tissue specimen is prepared for analysis. The preferred optimum biological sample for preparation in the apparatus of this invention is a fresh one cubic millimeter biopsy sample. This sample must be vitrified as soon as possible. By vitrifying or vitrification it is intended to make reference to a process which results in cryofixation of the sample which is different from "frozen." In the process of vitrifying, the cooling apparatus which is used renders a portion of the sample in the vitreous phase such that soluble and insoluble moieties contained in the tissue sample are not disturbed, translated, or altered nor are they concentrated (as eutectics). By definition, a vitrified liquid will shatter when undergoing a shear stress, e.g., window glass. The vitreous phase involves the conversion of liquid water into an amorphous or "glass" phase. This is accomplished by rapidly supercooling the tissue sample by opposing it "bounce-free" onto the highly polished (mirror-like) contaminate-free cryo-slam surface preferably at between $-265°$ C. and $-175°$ C. It is preferred that such rapid supercooling be completed in less than one second.

Depending on the anticipated time lag between supercooling of the sample and dehydration of the sample, the sample may be stored submerged in a liquid nitrogen dewar at $-196°$ C. Once the sample has been dried and embedded properly it may be stored virtually indefinitely without cytoplasmic reticulation or other forms of cellular catabolism which will cause modifications and crystal lattice transitions resulting in undesirable artifacts which render the tissue uninterpretable as analytical data.

As shown schematically in FIG. 14, the apparatus for ultrarapid cooling of this invention includes a cryogenic block having an upper cryo-slam surface 20 and a lower cryofinger 25. A vacuum source 30 functions to impart a vacuum to the atmosphere surrounding the cryo-slam surface 20. The apparatus further includes a source of fluid coolant 40 which functions to bring the cryo-slam surface 20 to cryogenic temperatures. A source of non-condensable dry inert gas 50 is also associated with the vacuum chamber 21 to raise the pressure surrounding the cryo-slam surface 20 prior to sample delivery. A sample delivery assembly 60 and a shutter assembly 61 are functionally associated with the cryo-slam surface 20 and include means for mounting biological tissue and means for transferring the biological tissue from outside of the chamber enclosing the cryogenic block to inside the chamber and into contact with cryo-slam surface 20. A thermocouple (not shown) is embedded at the interface of cryo-slam surface 20 and cryofinger 25. The thermocouple is connected to the wire 84 which leads outside the vacuum chamber 21 through a feedthrough 80. The thermocouple is associated with the cryogenic block to monitor the temperature of cryo-slam surface 20.

Figure 4:
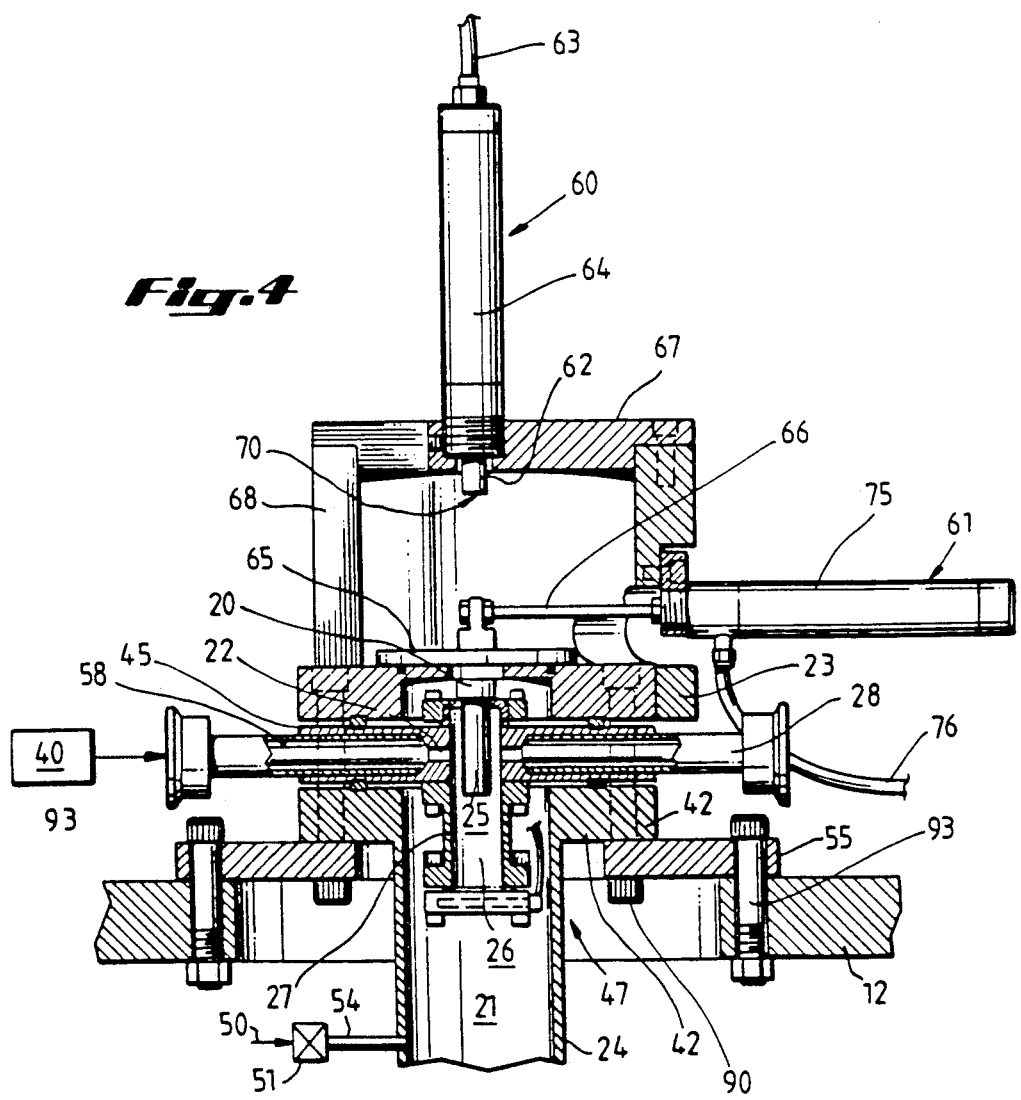
FIG. 4 is a cross-sectional view of the vacuum chamber and delivery assembly according to a preferred embodiment of the present invention, taken along section line 4—4 of FIG. 3.
Figure 8:
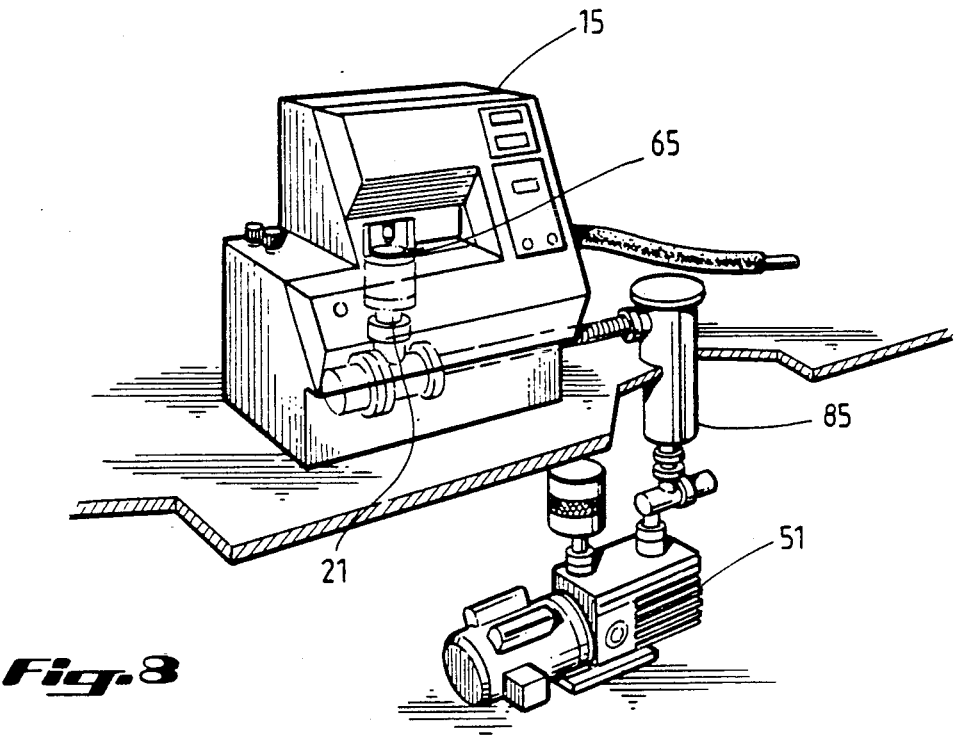
FIG. 8 is a perspective view of a preferred embodiment of the cryo-slamming apparatus according to the present invention showing the apparatus housing, combination trap and vacuum pump.

FIG. 1 is a perspective view of a preferred embodiment of the present invention. In this embodiment, major components of cryo-slamming apparatus include sample delivery assembly 60, vacuum chamber 21, a vacuum source 30, and controls 11. The cryo-slamming apparatus is mounted on mounting flange 55 which is fixed to horizontal surface 12 which is enclosed in apparatus housing 15 (FIG. 8). The sample delivery assembly 60 comprises a plunger 62 which is slideably mounted in plunger housing 64. At the end of the plunger is a sample holder 70 (FIG. 4). Pneumatic conduit 63 is connected to the plunger housing 64. The plunger 62 is pneumatically actuated to move the tissue specimen downward against the cryo-slam surface 20 when shutter 65 is pneumatically opened.

The sample delivery assembly 60 is mounted on base plate 67 which is supported over the vacuum chamber 21 by means of a circular sidewall 68. The sample delivery assembly is cooperatively aligned with the vacuum chamber 21 so that it may be actuated pneumatically to move the tissue specimen downward against a cryo-slam surface 20 when the shutter assembly 61 opens access to the vacuum chamber 21.

Figure 12:
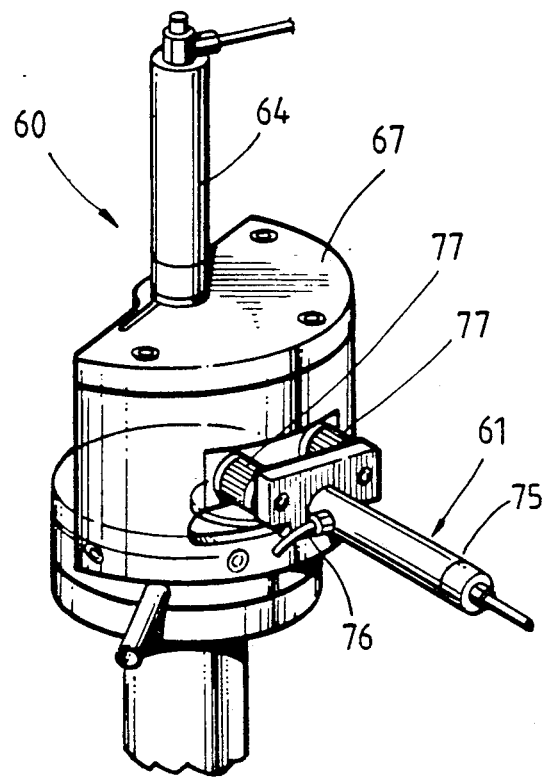
FIG. 12 is a perspective view of the vacuum chamber and delivery assembly according to an alternate preferred embodiment of the present invention.

The shutter assembly 61 comprises a shutter 65, which is mounted on rod 66 extending from rod housing 75. The shutter assembly 61 is pneumatically actuated. Pneumatic conduit 76 extends to the rod housing 75. The shutter 65 seals the vacuum chamber upper end plate 23, and moves the shutter to open the vacuum chamber when a sample is to be slammed against the cryogenic block. The shutter 65 is actuated pneumatically and is movable to open cooperatively with downward movement of plunger 62. The pneumatic actuation provides continuous force at a constant rate of descent to the plunger 62, with a functionally effective delay between the time shutter 65 is open until sample application against the cryo-slam surface 20. In most instances the delay will be less than 5 milliseconds. In a preferred embodiment, the shutter assembly 61 is associated with a flexible shock absorbing mount 77 (FIG. 12) which reduces shock waves to the cryo-slam surface 20 caused by pneumatic actuation of the shutter 65.

The vacuum chamber 21 includes upper end plate 23, conduit housing 45, and vacuum chamber housing 47. These components are mounted together in sealing relationship and are preferably composed of stainless steel and constructed so they may be vacuum sealed. In a preferred embodiment, the upper end plate 23 contains an access plate (not shown) which allows easy access to components located within the vacuum chamber 21. The access plate is concentric with the shutter opening and is associated with an o-ring seal to prevent leakage under vacuum conditions. A cryo-slam surface 20 (FIG. 14) is located within the vacuum chamber 21. A source of fluid coolant 40 is provided to cool the cryo-slam surface 20 via cooling inlet conduit 22 which is connected by cooling inlet coupling 38 to the conduit housing flange 45, which in the preferred embodiment is a two-sided conflat flange. Further, cooling outlet conduit 28 is connected by cooling outlet coupling 39 to an opposing side of the conduit housing 45. The inlet 22 and outlet 28 are used to circulate cooling fluids such as liquid nitrogen or helium to cool the cryogenic block prior to slamming a tissue sample against that surface.

Figure 9:
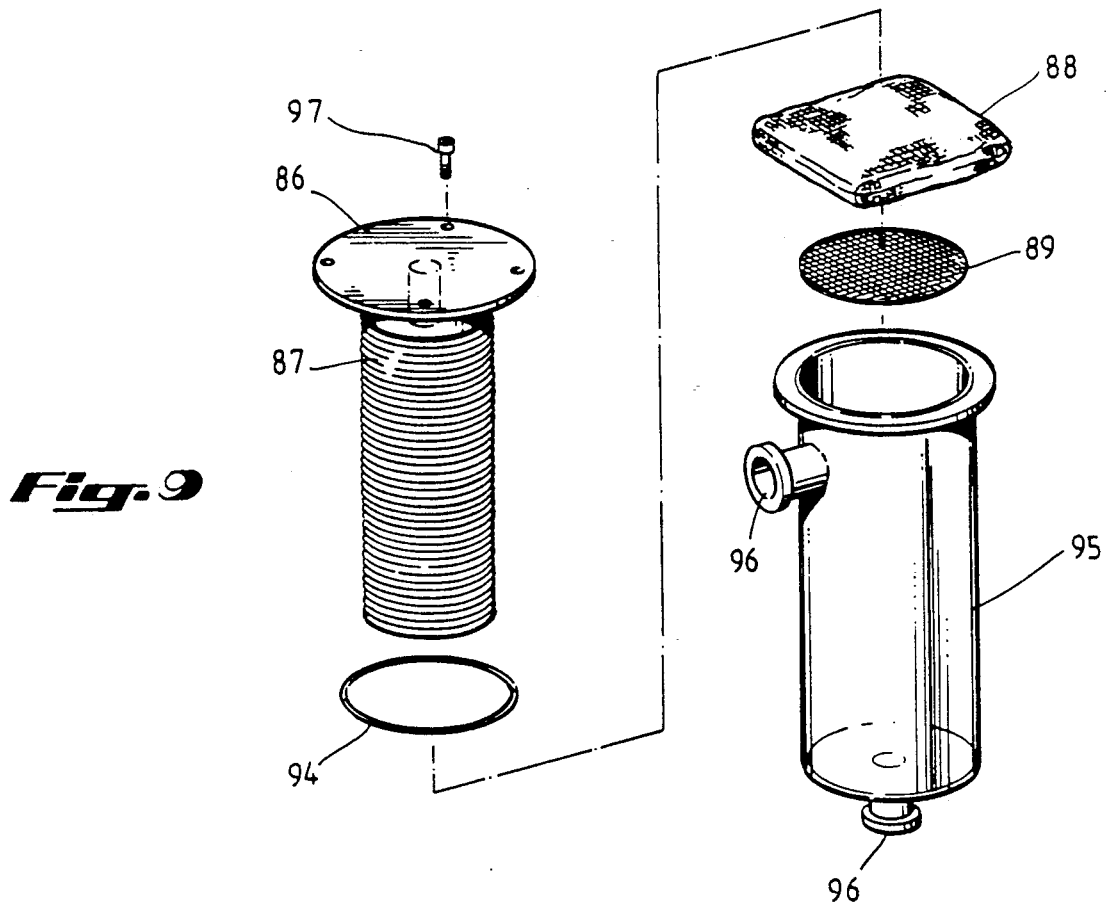
FIG. 9 is an exploded perspective view of a preferred embodiment of the combination trap according to the present invention.

The vacuum source 30 is connected to the lower end of vacuum chamber housing 47 with a vacuum coupling 34. The vacuum source 30 further includes vacuum valves 31 and vacuum conduit 56. Vacuum source 30 imparts a high hydrocarbon free vacuum to the vacuum chamber 21. In a preferred embodiment the vacuum source 30 includes a combination trap 85 (FIG. 8). FIG. 9 shows an exploded view of the combination trap with housing 95 having vacuum line connections 96. A molecular sieve 88 is inserted on top of screen 89. The fluid coolant reservoir and condensing surface 87 is inserted into housing 95 and sealed with o-ring 94. The combination trap upper end plate 86 is secured to the housing 95 with 4 screws 97. The fluid coolant reservoir may be filled with a coolant such as liquid nitrogen and the like. The molecular sieve consists of a desiccant such as a zeolite material or other conventional desiccant.

Continuing in FIG. 1, the dry inert gas source 50 is connected to vacuum reversal conduit 54 which is connected to vacuum chamber housing 47. The dry inert gas source 50 is also connected to vacuum reversal valve 51 to control vacuum reversal flow which, in the preferred embodiment, is dry helium or dry nitrogen gas at room temperature.

The temperature regulator or thermocouple (not shown) includes electrical leads extending through conduit 83 which is connected to conduit housing 45 to monitor the temperature of the cryo-slam surface 20 (FIG. 4). An electrical connector 82 for the heating unit and an electrical connector 84 for the thermocouple extend from the conduit housing 45 through electrical conduit 83.

FIG. 2 shows a perspective view of a preferred embodiment of the vacuum chamber and delivery assembly. According to a preferred embodiment of the present invention, the vacuum chamber 21 is shown with the sample delivery assembly 60 cooperatively mounted above the chamber. As shown, sample delivery assembly 60 includes pneumatic conduit 63 and plunger housing 64. Plunger housing 64 is mounted on base plate 67 and circular sidewall 68 above the sample chamber 21. Also shown in FIG. 2 is rod housing 75 mounted into the side of circular sidewall 68. Pneumatic conduit 76 is connected to the rod housing 75, along with pneumatic conduit 76 to provide pneumatic force to the rod connected to the shutter opening the vacuum chamber 21. Also shown in FIG. 2 is mounting flange 55 which is mounted on the horizontal surface 12.

In FIG. 3, a top view of the vacuum chamber according to the preferred embodiment of the present invention is shown. In the top view, base plate 67 can be seen mounted above the upper end plate 23 of the vacuum chamber. Also shown in FIG. 3 is a mounting flange 55 and rod housing 75. Shutter 65 seals the top of the vacuum chamber upper end plate 23. Additionally FIG. 3 shows the cooling inlet conduit 22 and the cooling outlet conduit 28 for cooling the cryogenic block mounted within the vacuum chamber 21.

Figure 13:
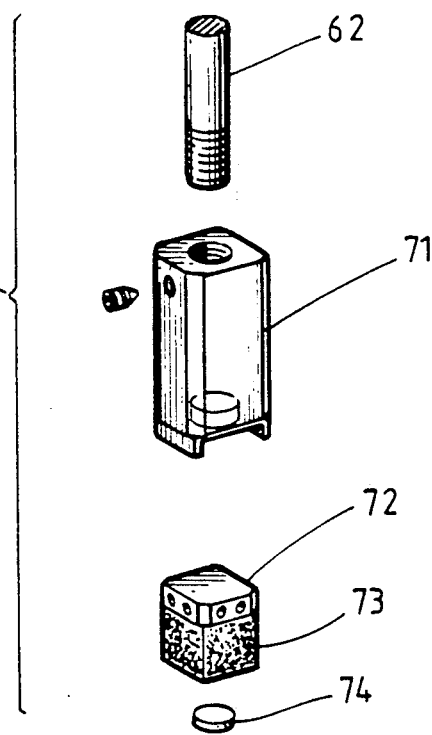
FIG. 13 is an exploded view of the sample holder according to a preferred embodiment of the present invention.

FIG. 4 is a cross sectional view of the vacuum chamber and delivery assembly according to a preferred embodiment of the present invention. FIG. 4 is taken along section line 4—4 of FIG. 3. As shown, sample delivery assembly 60 includes plunger housing 64, plunger 62 extending from the plunger housing and terminating at sample holder 70. In FIG. 13, the plunger 62 is connected to plunger head 71 which is adapted to receive the sample holder. The sample holder includes a metal base 72 connected to foam backing 73 upon which the sample 74 is mounted. This sample holder design minimizes compressive distortion of the tissue specimen. In a preferred embodiment, an insulator such as Thermanox ® is used as the sample backing to retard the transfer of conductive heat from the sample holder. Continuing in FIG. 4, the sample delivery assembly also includes pneumatic conduit 63. The sample delivery assembly is mounted on base plate 67 extending from the top of the circular sidewall 68 which is mounted on upper end plate 23 of the vacuum chamber 21. Vacuum chamber 21 comprises upper end plate 23, conduit housing 45 and vacuum chamber housing 47. These components are sealed together in sealing engagement with vacuum chamber screws 90. Shutter 65 seals the opening of upper end plate 23 and is connected to rod 66 extending from rod housing 75. The shutter assembly 61 comprises shutter 65, rod 66, rod housing 75 and pneumatic conduit 76. The rod housing 75 is mounted on circular sidewall 68, and is pneumatically actuated to move the shutter to open the vacuum chamber 21.

A source of fluid coolant 40 (see FIG. 14) supplies cryogenic cooling fluid to inlet conduit 22, through cooling jacket chamber 26 and out the outlet conduit 28. Cooling jacket 27 is mounted within the vacuum chamber 21. The cooling jacket 27 holds the lower region ("cryofinger") 25 of the cryogenic block. The cryofinger 25 extends into the cooling jacket chamber 26 which is supplied with fluid such as liquid nitrogen or helium during the cooling process. In a preferred embodiment, cooling jacket 27 includes a bellows member 19 (FIG. 10) which reduces fatigue caused by thermal contraction and expansion during the consecutive slamming of tissue specimens. Vacuum jacket 58 thermally isolates cryogenic effects of the liquid coolant from all but the cryogenic components of the apparatus, i.e., the cryogenic block.

The cryo-slam surface 20 may be composed of copper, chromium, gold, silver, diamond or sapphire or combinations thereof or other suitable means having high heat conductivity at low temperatures and providing a mirror finished flat smooth surface for contact with tissue samples. Preferred cryo-slam surfaces include copper with a sapphire outer portion or copper with a diamond outer portion. Oxidation of a copper surface occurs rapidly when exposed to the atmosphere. It is desirable to reduce any oxidation of the cryo-slam surface which would result in reduced thermal conductivity. Therefore, the cryo-slam surface is preferably double gold-plated copper which reduces oxidation of its surface and eliminates the need for repeated polishing. Most preferably, the cryo-slam surface 20 is copper plated with $5\mu$ inch acid gold and $45\mu$ inch alkaline gold. The preferred cryofinger 25 is 100% copper and is maintained within cooling jacket chamber 26. In a preferred embodiment, the cryo-slam surface 20 may be removed from the cryofinger 25 for cleaning or replacement with a cryo-slam surface having an alternate shape or composition.

Still referring to FIG. 4, the vacuum chamber housing 47 comprises vacuum chamber housing flange 42, and vacuum chamber housing sidewall 24. A source of dry inert gas 50 is attached to supply a dry helium or nitrogen gas to the vacuum chamber 21. The inert gas source 50 is connected to vacuum reversal valve 51 and vacuum reversal conduit 54. The vacuum chamber housing flange 42 is mounted on mounting flange 55 and affixed by mounting flange screw 93 on the horizontal surface 12.

FIG. 5 shows the vacuum chamber 21 and cooling jacket 27 in more detail. As shown in FIG. 5, shutter 65 seals the top of upper end plate 23. The shutter 65 is opened when the rod 66 is pneumatically actuated to move the shutter 65 out of sealing relationship with the upper end plate 23. An o-ring 37 is included in the upper end plate 23 for sealing with the shutter 65. The cryo-slam surface 20 is shown in FIG. 5 connected to the cryofinger 25 maintained within the cooling jacket chamber 26. The cooling jacket 27 further includes cooling jacket upper end plate 29 and cooling jacket lower end plate 44. Cooling jacket 27 is sealed to the lower side of conduit housing 45, while cooling jacket upper end plate 29 is sealed to the top of the conduit housing 45. Upper cooling jacket screw 91 connects the cooling jacket 27 and conduit housing 45. Cooling jacket 27 further includes cooling jacket upper flange 52 and lower flange 53. The lower flange 53 is connected to cooling jacket lower end plate 44 with lower cooling jacket screw 92. Cooling jacket chamber 26 is sealed to hold a fluid coolant such as liquid nitrogen or helium which is circulated through the cooling jacket 27. This is the only known slamming device that can withstand 20 p.s.i. of coolant pressure for rapid cooling of the cryo-slam surface, most prior art devices are effective at no more than 2-5 p.s.i.

Also shown in FIG. 5, a source of fluid coolant 40 supplies cryogenic fluid through cooling inlet conduit 22 which introduces the fluid into the cooling jacket chamber 26 and out the cooling outlet conduit 28. Conduits 22 and 28 are surrounded by vacuum conduit 58. Also shown in FIG. 5 is vacuum chamber housing 47 which is mounted on mounting flange 55 with vacuum chamber screws 90. A source of dry inert gas 50 supplies a noncondensable gas such as dry helium or nitrogen through vacuum reversal conduit 54, controlled by valve 51, which provide access through vacuum chamber housing sidewall 24. The type and temperature of the gas used for vacuum reversal are independently variable.

Now turning to FIG. 6, a cross sectional view of the conduit housing 45 according to a preferred embodiment of the present invention is shown, taken along section line 6—6 of FIG. 5. As shown in FIG. 6, conduit housing 45 includes cooling inlet conduit 22 and cooling outlet conduit 28. The inlet conduit and outlet conduit are surrounded by vacuum conduit 58. Also shown in FIG. 6 is conduit housing orifice 57 which is a portion of the vacuum chamber 21. Thus, the vacuum chamber 21 extends both below and above the conduit housing 45.

FIG. 7 is an exploded perspective view of the vacuum chamber 21 according to a preferred embodiment of the present invention. As shown in FIG. 7, shutter 65 is removably connected to rod 66, which seals off the aperture 36 in the vacuum chamber upper end plate 23. A seal or o-ring 37 is provided within concentric groove 35 in the vacuum chamber upper end plate 23. The upper end plate 23 comprises the top portion of vacuum chamber 21 (FIG. 5). Due to the extreme temperature and pressure conditions, the o-ring 37 may be manufactured of special materials to assure a seal. A conflat flange copper gasket 46 is used to seal the vacuum chamber upper end plate 23 against the conduit housing 45. The cryo-slam surface 20 is removably connected to cryofinger 25 which is maintained within cooling jacket 27 (FIG. 5). An electrical connector 82 for the heating unit extends from the cryofinger 25. An electrical connector 84 for an embedded thermocouple extends from the cryofinger. Electrical connectors 82 and 84 extend outside vacuum chamber housing 47 through grommet 80 (FIG. 14). The cryofinger 25 of the cryogenic block houses a heating unit which in the preferred embodiment is heating element or cartridge heater 81. The heating element of cartridge heater 81 is shown in FIG. 11.

Figure 10:
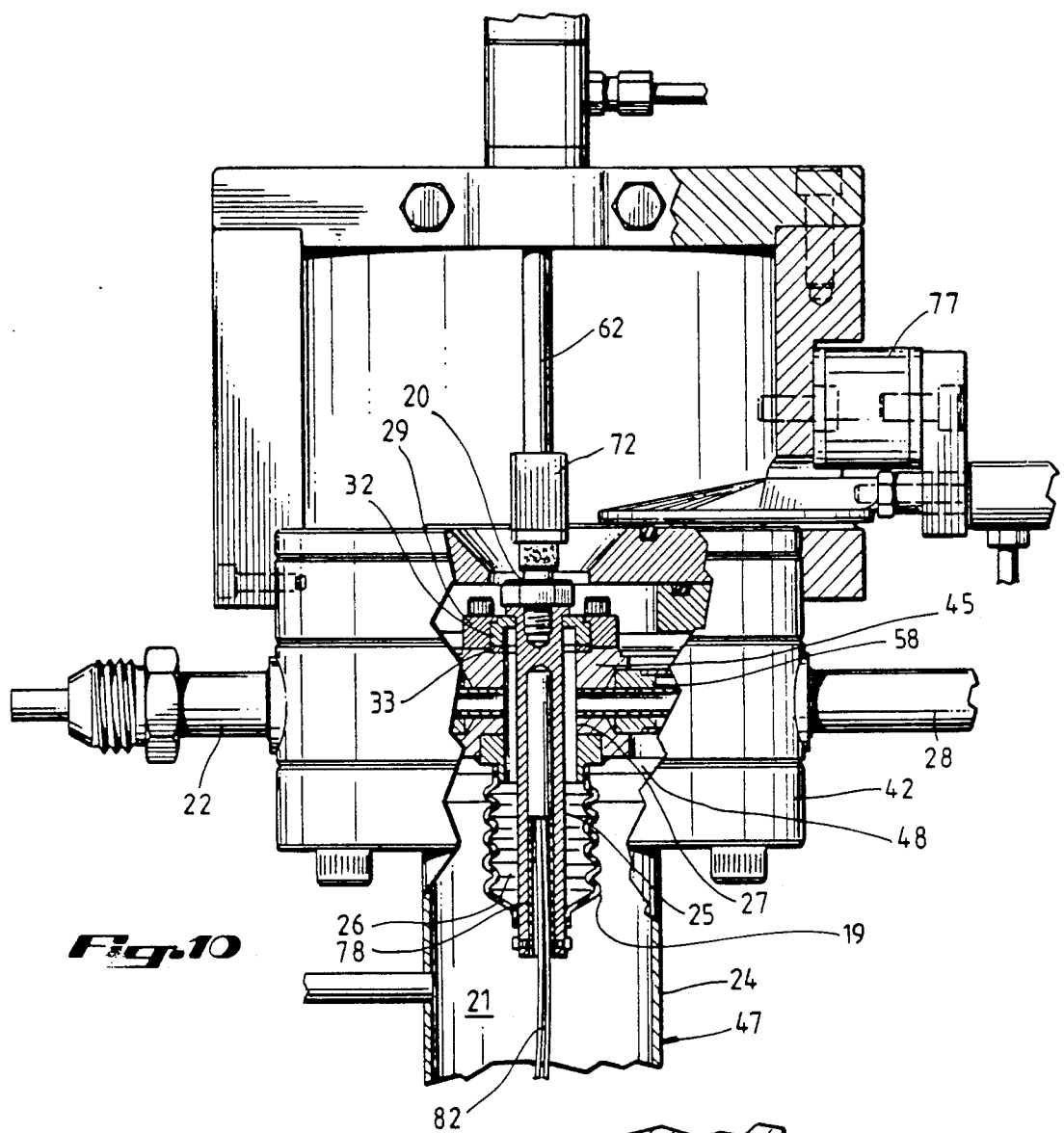
FIG. 10 is an interior view of the vacuum chamber according to an alternate preferred embodiment of the present invention.
Figure 11:
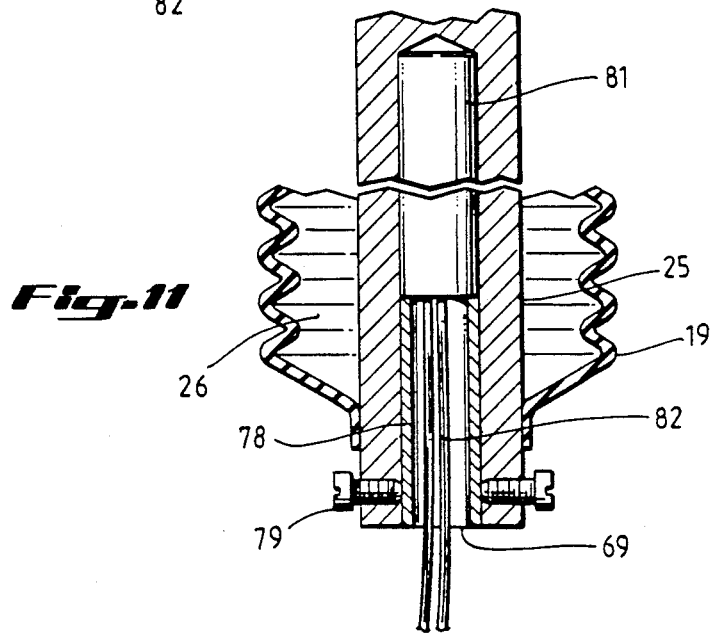
FIG. 11 is an exploded interior view of the lower cooling jacket according to the embodiment of the present invention shown in FIG. 10.

In FIG. 11, the heating element or cartridge heater 81 is connected to electrical connector 82, preferably having a temperature regulator. Heating element or cartridge heater 81 thus enables automatic regeneration of the cryo-slam surface 20 (FIG. 10) for rapid turnover of samples. The heating element or cartridge 81 may be used to regulate the temperature of the cryo-slam surface 20, depending upon the temperature desired for slamming the particular tissue specimen. Heating element or cartridge heater 81 is housed in the cryofinger 25 (FIG. 10) by conventional fastening means. In a preferred embodiment (FIGS. 10-11), the cryofinger 25 extends below the cooling jacket 27 (bellows member 19) and into the vacuum chamber 21. The lower surface of cryofinger 25 contains orifice 69 which becomes an inner cavity fashioned to enclose the heating unit 81. The heating unit 81 may be secured within the inner cavity of cryofinger 25 by an interference fit or, as shown in FIG. 11, may be further secured by a back-up cylinder 78 and set-screws 79. This arrangement allows easy access to the heating unit for replacement purposes. Moreover, the electrical connector 82 is thermally insulated from the cooling fluid in chamber 26 which increases the operational life of the heating unit 81. Heating element 81 is electrically connected to energy means, not shown, by electrical connector 82. A thermocouple is embedded within the upper portion of cryofinger 25 to monitor the temperature of the cryo-slam surface 20.

In FIG. 10, the cooling jacket 27 is enclosed within the vacuum chamber 21. The cooling jacket 27 comprises cooling jacket upper end plate 29, annular cooling jacket seal 32, and a copper gasket 33 for sealing the upper end plate 29 with the upper surface of conduit housing 45. The cryofinger 25 is slideably mounted within the cooling jacket upper end plate 29 and bonded with the annular cooling jacket seal 32. Thus, the cooling jacket chamber 26 is sealed from the vacuum chamber 21 while the cryo-slam surface 20 extends from the top of the cooling jacket 27. Also shown are conduit housing 45 having conduit housing orifice 57 (FIG. 7) extending therethrough, along with the fittings necessary to receive cooling inlet conduit 22 and cooling outlet conduit 28, which circulates a fluid coolant through the cooling jacket chamber 26. The conduit housing orifices 57 are part of the vacuum chamber 21. Conflat flange copper gasket 48 is provided to seal the conduit housing 45 with the vacuum chamber flange 42 of the vacuum chamber housing 47. The vacuum chamber housing 47 further includes vacuum chamber housing sidewall 24 and bottom surface of housing 49 (FIG. 7).

Now referring to FIG. 7 the cooling jacket 27, copper gasket 43 seals the cooling jacket body upper flange 52 with the conduit housing 45. Copper gasket 41 seals the cooling jacket lower flange 53 to the cooling jacket lower end plate 44. Thus, the cooling jacket 27 is tightly sealed within the vacuum chamber 21. Upper cooling jacket screw 91 and lower cooling jacket screw 92 are provided to assemble the cooling jacket with the conduit housing 45. Vacuum chamber screws 90 further are provided to assemble the vacuum chamber upper end plate 23, conduit housing 45 and vacuum chamber housing 47.

An external vacuum pump 59 (FIG. 8) is utilized to create a vacuum in vacuum chamber 21. The vacuum pump 59 is preferably a vibration isolated cryosorption pump or vane pump or equivalent device for creating a vacuum of at least $10^{-4}$ mbar in the chamber 21. The vacuum pump 59 can be any of a variety of commercially available pumping apparatus.

In FIG. 14, the cooling jacket 27 is provided with inlet conduit 22 for conveying fluid coolant from a reservoir to vacuum chamber 21. Additionally, the cooling jacket 27 is provided with outlet conduit 28 for purging the cooling fluid. An external source of coolant with controls is used to regulate the supply of coolant to cooling jacket 27. The fluid coolant may be selected from liquid nitrogen, liquid helium and the like. One advantage of the apparatus and method of the invention is the ability to supply cooling fluids at substantially increased pressures than prior art devices. Cooling fluids are typically supplied at a pressure from about 10-25 psi, preferably of at a pressure of 15-20 psi and most preferably at 20 psi.

In FIG. 8, the operation of the present invention in the preferred embodiment is set forth below. Initially, the shutter 65 enclosing the vacuum chamber 21 is closed. The vacuum pump 59 is actuated to secure a high vacuum in the vacuum chamber 21. Once a vacuum has been reached in the vacuum chamber 21, cooling fluid is introduced to the cooling jacket 27 through cooling inlet conduit 22 and out the cooling outlet 28 (FIG. 14). A source of fluid coolant 40 is used to cool the cryo-slam surface 20 (FIG. 14) to a temperature of preferably $-175°$ C. or below. The particular temperature for the cryo-slam surface 20 (FIG. 14) may be varied according to the present invention. The temperature desired depends on factors such as the composition of the cryo-slam surface and the tissue specimen. A thermocouple (not shown) is used to sense the temperature of the cryo-slam surface during the cooling process.

When the desired temperature is reached the vacuum source 30 (FIG. 14) is isolated and a dry inert gas 50 is introduced to reverse the vacuum within the vacuum chamber 21. In FIG. 14, the gas must be noncondensable at the cryogenic block temperature. In a preferred embodiment, dry helium gas is used to reverse the vacuum. Alternatively, dry nitrogen gas at room temperature may be used. Vacuum reversal valve 51 and conduit 54 are used to allow dry helium gas or dry nitrogen gas at room temperature to enter the vacuum chamber 21 and raise the pressure inside the chamber to atmospheric pressure. The use of noncondensable dry helium gas or dry nitrogen gas at room temperature prevents precooling of the tissue specimen during movement towards cryo-slam surface 20. It should be understood that any other noncondensable inert gas may be used, preferably at room temperature, to raise the pressure inside the vacuum chamber 21 without undesirable condensation on the cryo-slam surface 20 or precooling of the tissue specimen. When the vacuum chamber 21 reaches atmospheric pressure, wherein the pressure inside of the shutter 65 equals the outside of the shutter, the shutter 65 is pneumatically actuated to open the access to the vacuum chamber 21. Pneumatic actuation provides a constant rate of descent of the plunger 62 through the opening in the vacuum chamber upper end plate 23 and against the cryo-slam surface 20. The fluid coolant source 40 and vacuum pump 59 are turned off during the slamming of the tissue sample against the cryo-slam surface 20, so that the cooling fluid will not impart any undesired vibration to the cooling surface during the slamming process. Preferably, the sample is maintained against the cryo-slam surface for about 10 seconds to effectively establish thermal inertia in the sample and sample holder prior to removal.

Preferably there is a functionally effective delay between the opening of the chamber via the pneumatic shutter and the slamming of the tissue sample against the cryo-slam surface. At the time of application of the sample, the cryo-slam surface preferably is a temperature of $-265°$ C. to $-175°$ C., depending upon the particular fluid coolant means employed.

In FIG. 40, after the sample is plunged or slammed against the cryo-slam surface 20, the fluid coolant source 40 may be reactuated. After slamming, the tissue specimen may remain in contact with the cryo-slam surface 20 for a desired period of time. Optionally at this point the tissue specimen may be removed from the cryo-slam surface 20 and placed in a liquid nitrogen dewar for storage and maintained at a cool temperature after it is removed from the sample holder. The pneumatic shutter is then closed against the upper end plate 23. The heating unit 81 is then activated to raise the temperature of the cryo-slam surface 20. It is preferred that the shutter 65 be closed and a vacuum drawn during heating of the surface to reduce the amount of condensation and/or contaminants deposited on the cryo-slam surface 20. The heating step is accomplished under vacuum conditions to allow sublimation without contamination. When the cryo-slam surface 20 reaches the desired temperature, preferably room temperature, the cryogenic surface 20 may be cleaned. During the regeneration of the cryo-slam surface, the source of fluid coolant is shut off so that the desired temperature may be reached.

Now referring to the vacuum reversal step, the vacuum reversal valve 51 is actuated only to raise the pressure inside the vacuum chamber 21 to atmospheric pressure prior to slamming the sample against the cryo-slam surface 20. The vacuum reversal valve 51 is deactivated as soon as atmospheric pressure is reached. Optionally, after the sample is slammed against the cryo-slam surface 20 and removed from the cryo-slam surface 20, vacuum pump 59 is re-actuated to obtain a vacuum in the vacuum chamber 21 during regeneration of the cryo-slam surface.

In the past, the turnaround time between each sequential tissue specimen has been slow, due to the time for heating the block and reactivating the entire cooling system. In the present invention the turnaround regeneration time is reduced to between 3–5 minutes or less.

According to the present invention it is possible to cryo-slam (i.e., vitrify) a large number of tissue specimens sequentially after regenerating the cryo-slam surface between each sample. The cryo-slam surface is heated to preferably room temperature, cleaned and rapidly recooled between each tissue specimen. During cooling, the cryo-slam surface is in a high hydrocarbon free vacuum. The condensation on the cryo-slam surface and/or contamination of the cryo-slam surface does not occur prior to application of the tissue sample. Precooling of the sample and condensation on the cryo-slam surface is prevented by introducing room temperature dry helium gas, dry nitrogen inert gas, or other noncondensable gas at room temperature, into the vacuum chamber. The present invention also eliminates problems of vibration to the cryo-slam surface due to movement of cooling fluid or liquid helium and helium gas proximate to the surface before slamming. The pneumatic shutter and sample delivery assembly also eliminate problems of timing between opening of the shutter and slamming the tissue specimen against the cryo-slam surface.

In a preferred embodiment, the cryo-slamming apparatus of the present invention is associated with a microprocesser. The microprocesser may be adapted to control functions such as: vacuum chamber pressure, cryogenic block temperature, process timing of the plunger and shutter, and sample-cryogenic block dwell time.

Although the preferred embodiment of this invention has been described hereinabove in some detail, it should be appreciated that a variety of embodiments will be readily available to a person designing such cryopreparation apparatus for a specific end use. The description of the apparatus of this invention is not intended to be limiting on this invention, but is merely illustrative of the preferred embodiment of this invention. Other apparatus and components which incorporate modifications or changes to that which has been described herein are equally included within this application.

What is claimed is:

1. Apparatus for cryo-slamming a tissue specimen comprising:
   a. a cryogenic block comprising a detachable cryo-slam surface and a cryofinger, said cryo-slam surface comprising a highly polished and mirror-finished face adapted to receive a tissue specimen;
   said cryofinger comprising:
      (1) a thermally conductive tubular member and a thermally conductive closure member closing one end of said tubular member, said closure member being adapted to detachably secure said cryo-slam surface to said cryofinger;
      (2) an orifice extending within the other open end of the tubular member and defining an inner cavity; said inner cavity conformed to enclose a heating unit;
   b. a cooling jacket jacketing at least part of said tubular member but not the open end of the tubular member and capable of containing a fluid coolant;
   c. an evacuatable chamber housing said cryogenic block and said cooling jacket;
   d. a vacuum line connected to the evacuatable chamber and adapted to be connected to a source of vacuum;
   e. a cryogenic condenser in the vacuum line adapted to cool fluids passing through the vacuum line; and
   f. a molecular sieve trap in the vacuum line.

2. The apparatus of claim 1 wherein said cryo-slam surface is copper, chromium, gold, silver, sapphire, diamond or combinations thereof.

3. The apparatus of claim 1 wherein said cryo-slam surface is gold plated copper.

4. The apparatus of claim 3 wherein said cryo-slam surface is plated with about 5μ inch acid gold and about 45μ inch alkaline gold.

5. The apparatus of claim 1 wherein said cryo-slam surface is generally semispherical in shape and adapted to receive a cornea.

6. The apparatus of claim 1 which includes a thermocouple embedded in the closure member of said cryofinger.

7. The apparatus of claim 1 wherein said cryo-slam surface is substantially free of oxides and hydrocarbons.

8. The apparatus of claim 1 wherein said cryo-slamming is to a temperature of about −140° C. or below.

9. The apparatus of claim 1 wherein said cryo-slamming is to a temperature of about −180° C. or below.

10. The apparatus of claim 1 wherein said heating unit comprises an electrical heater.

11. The apparatus of claim 10 wherein said electrical heater is adapted for an interference fit with the inner cavity of said cryofinger.

12. The apparatus of claim 1 wherein said heating unit comprises an electrical heater enclosed within a back-up cylinder, said back-up cylinder being adapted for an interference fit with the inner cavity of said cryofinger.

13. The apparatus of claim 12 wherein said backup cylinder is further secured within the inner cavity of said cryofinger by set screws.

14. The apparatus of claim 10 wherein said electrical heater includes electrical leads connected at one end and leading out the open end of said tubular member whereby said electrical leads are thermally insulated from the fluid coolant within said cooling jacket.

15. The apparatus of claim 1 wherein said evacuatable chamber is attached to a source of vacuum sufficient to create a vacuum from about $1 \times 10^{-4}$ mbar to $1 \times 10^{-10}$ mbar.

16. The apparatus of claim 1 wherein said evacuatable chamber is attached to a source of dry inert gas operable to increase the pressure of the atmosphere surrounding said cryo-slam surface.

17. The apparatus of claim 1 wherein said molecular sieve trap comprises a zeolite bag charge.

18. The apparatus of claim 1 wherein said cooling jacket is adapted to contain a fluid coolant at a pressure from about 10 to about 20 pounds per square inch.

19. The apparatus of claim 1 wherein said cooling jacket includes a bellows member adapted to reduce fatigue resulting from repeated thermal contraction and expansion.

20. The apparatus of claim 1 wherein said fluid coolant is liquid nitrogen or liquid helium.

21. The apparatus of claim 1 further comprising a sample delivery assembly including a pneumatically operated plunger mounted in a support structure, said plunger being movable into and out of said evacuatable chamber, said support structure being cooperatively engaged to said evacuatable chamber, said plunger being cooperatively aligned with said cryo-slam surface such that said plunger's path of travel permits said plunger and the tissue specimen attached thereto to penetrate into said evacuatable chamber and into a mated position with said cryo-slam surface.

22. The apparatus of claim 21 wherein said sample delivery assembly further includes a movable shutter, said shutter controlling access of said plunger into said evacuatable chamber, the shutter-plunger system being cooperatively timed to allow minimum exposure of the cryo-slam surface during sample delivery.

23. The apparatus of claim 22 wherein said shutter includes a flexible shock absorbing mount operable to reduce shock waves on the cryo-slam surface.

24. The apparatus of claim 21 wherein said sample delivery assembly further includes a sample holder, said sample holder being characterized by construction which minimizes compression and bounce upon contact with said cryo-slam surface.

25. The apparatus of claim 24 wherein said sample holder includes a magnetic disk, a foam rubber cushion; a brass plate; and mounting means for said tissue specimen.

26. The apparatus of claim 1 which includes a microprocessor adapted to control functions including pneumatic plunger actuation, shutter delay, plunger-cryo-slam surface dwell time, and cryo-slam surface temperature.

27. The apparatus of claim 1 which includes a manual override control operable to override microprocessor functions and pneumatically actuated functions.

28. Apparatus for cryo-slamming a tissue specimen comprising:
  a. a cryogenic block comprising a detachable cryo-slam surface and a cryofinger, said cryo-slam surface comprising a highly polished and mirror-finished face adapted to receive a tissue specimen; said cryofinger comprising a thermally conductive tubular member and a thermally conductive closure member closing one end of said tubular member, said closure member being adapted to detachably secure said cryo-slam surface to said cryofinger;
  b. a heating unit adapted to be removably inserted into the other open end of said tubular member;
  c. a cooling jacket jacketing at least part of said tubular member but not the open end of the tubular member and capable of containing a fluid coolant;
  d. an evacuatable chamber housing said cryogenic block and said cooling jacket;
  e. a vacuum line connected to the evacuatable chamber and adapted to be connected to a source of vacuum;
  f. a cryogenic condenser in the vacuum line adapted to cool fluids passing through the vacuum line; and
  g. a molecular sieve trap in the vacuum line.

29. Apparatus for cryo-slamming a tissue specimen comprising:
  a. a cryogenic block comprising a detachable cryo-slam surface and a cryofinger, said cryo-slam surface comprising a highly polished and mirror-finished face adapted to receive a tissue specimen; said cryofinger comprising a thermally conductive tubular member and a thermally conductive closure member closing one end of said tubular member, said closure member being adapted to detachably secure said cryo-slam surface to said cryofinger;
  b. an electrical heater adapted to be removably inserted into the other open end of said tubular member;
  c. a cooling jacket jacketing at least part of said tubular member but not the open end of the tubular member and capable of containing a fluid coolant;
  d. an evacuatable chamber housing said cryogenic block and said cooling jacket;
  e. a vacuum line connected to the evacuatable chamber and adapted to be connected to a source of vacuum;
  f. a cryogenic condenser in the vacuum line adapted to cool fluids passing through the vacuum line;
  g. a molecular sieve trap in the vacuum line;
  h. a source of dry inert gas connected to the evacuatable chamber and operable to increase the pressure of the atmosphere surrounding said cryo-slam surface; and
  i. electrical leads connected at one end to the electrical heater and leading out the open end of said tubular member whereby said electrical leads are thermally insulated from fluid coolant within said cooling jacket.

30. Apparatus for cryo-slamming a tissue specimen comprising:
  a. a cryogenic block adapted to receive tissue specimen and to ultrarapidly cool the same, said cryogenic block being enclosed within a chamber;
  b. vacuum means functionally attached to said chamber and adapted to reduce the pressure of the atmosphere surrounding said cryogenic block;
  c. cooling means functionally associated with said cryogenic block and said chamber;
  d. vacuum reversal means functionally associated with said chamber to increase the pressure of the atmosphere surrounding said cryogenic block;

e. a combination trap functionally attached to said vacuum means and said chamber comprising a cryogenic condenser and a molecular sieve and adapted to reduce hydrocarbon build up on said cryogenic block;

f. a sample delivery assembly functionally associated with said cryogenic block and said chamber, said assembly including means for mounting said tissue specimen and means adapted to transfer said tissue specimen from outside said chamber to said cryogenic block inside said chamber; and g. heating means functionally associated with said cryogenic block, said heating means being effective to permit rapid regeneration of said cryogenic block.

* * * * *